US012551334B2

(12) United States Patent
Hoang et al.

(10) Patent No.: US 12,551,334 B2
(45) Date of Patent: Feb. 17, 2026

(54) SURGICAL IMPLANT DELIVERY WITH LOCKABLE PLUNGER

(71) Applicant: Alcon Inc., Fribourg (CH)

(72) Inventors: Harlen Hoang, Fort Worth, TX (US); Yinghui Wu, Cedar Hill, TX (US); R. Mitchell Sherry, Fort Worth, TX (US); Sudarshan B. Singh, Euless, TX (US)

( * ) Notice: Subject to any disclaimer, the term of this patent is extended or adjusted under 35 U.S.C. 154(b) by 449 days.

(21) Appl. No.: 18/048,576

(22) Filed: Oct. 21, 2022

(65) Prior Publication Data

US 2023/0131381 A1 Apr. 27, 2023

Related U.S. Application Data

(60) Provisional application No. 63/263,099, filed on Oct. 27, 2021.

(51) Int. Cl.
*A61F 2/16* (2006.01)

(52) U.S. Cl.
CPC .................................... *A61F 2/167* (2013.01)

(58) Field of Classification Search
CPC ........ A61M 5/178; A61F 2/167; A61F 2/1678
See application file for complete search history.

(56) References Cited

U.S. PATENT DOCUMENTS 5,873,879 A 2/1999 Figueroa et al.
7,156,854 B2 1/2007 Brown et al.
8,105,332 B2 1/2012 Downer et al.
8,377,076 B2 2/2013 Downer et al.
10,568,735 B2 2/2020 Brown et al.
10,588,780 B2 3/2020 Van Noy et al.
11,039,953 B2 6/2021 Balachandran
12,004,944 B2 6/2024 Weston
2008/0147081 A1 6/2008 Pynson
2008/0221584 A1* 9/2008 Downer ................ A61F 2/1678 606/107
2010/0057093 A1 3/2010 Ide et al.
2010/0125278 A1 5/2010 Wagner
2011/0265779 A1 11/2011 Vandrak et al.
2012/0022548 A1 1/2012 Zacharias
(Continued)

FOREIGN PATENT DOCUMENTS

JP 2007190360 A 8/2007
JP 2007244570 A 9/2007
(Continued)

OTHER PUBLICATIONS

Feb. 6, 2023 International Search Report and Written Opinion of the International Searching Authority PCT/IB2022/060155.

*Primary Examiner* — Anh T Dang
(74) *Attorney, Agent, or Firm* — Darin Deaver

(57) ABSTRACT

An apparatus for eye surgery comprising a housing comprising a key track, a bore through the housing, a plunger at least partially disposed in the bore, and a plunger key. The plunger may comprise a rail and a keyway, and the plunger key may comprise a key guide coupled to the key track, an arm coupled to the key guide, and a rail slot through the arm. The arm may be disposed through the keyway of the plunger to allow the arm to move along the key track from a first position to a second position. The arm may be configured to block the rail in the first position and to align the rail slot with the rail in the second position so that the rail can move through the rail slot.

18 Claims, 10 Drawing Sheets

(56) References Cited

U.S. PATENT DOCUMENTS

| | | | |
|---|---|---|---|
| 2013/0253527 | A1 | 9/2013 | Schneider et al. |
| 2014/0257315 | A1 | 9/2014 | Wu |
| 2015/0238687 | A1 | 8/2015 | Novakovic et al. |
| 2015/0282928 | A1 | 10/2015 | Auld et al. |
| 2016/0087460 | A1 | 3/2016 | Rich et al. |
| 2017/0007237 | A1 | 1/2017 | Yates et al. |
| 2017/0119522 | A1 | 5/2017 | Auld et al. |
| 2017/0135811 | A1 | 5/2017 | Springer et al. |
| 2018/0049866 | A1 | 2/2018 | Fayyaz et al. |
| 2018/0200046 | A1* | 7/2018 | Brown .................. A61F 2/1691 |
| 2018/0200047 | A1 | 7/2018 | Wu et al. |
| 2020/0015959 | A1 | 1/2020 | Wensrich et al. |
| 2020/0038171 | A1 | 2/2020 | Glick et al. |
| 2021/0038369 | A1 | 2/2021 | Holderby |
| 2021/0052371 | A1 | 2/2021 | Singh et al. |
| 2022/0265420 | A1 | 8/2022 | Kelp |

FOREIGN PATENT DOCUMENTS

| | | | |
|---|---|---|---|
| JP | 2016503716 | A | 2/2016 |
| WO | 2006059183 | A1 | 6/2006 |
| WO | 2016141308 | A1 | 9/2016 |
| WO | 2020128762 | A1 | 6/2020 |

* cited by examiner

SURGICAL IMPLANT DELIVERY WITH LOCKABLE PLUNGER

PRIORITY CLAIM

This application claims the benefit of priority of U.S. Provisional Patent Application Ser. No. 63/263,099 titled "SURGICAL IMPLANT DELIVERY WITH LOCKABLE PLUNGER," filed on Oct. 27, 2021, whose inventors are Harlen Hoang, Yinghui Wu, Mitchell R. Sherry and Sudarshan B. Singh, which is hereby incorporated by reference in its entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies, which can cause mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may provide a housing comprising a key track, a bore through the housing, a plunger at least partially disposed in the bore, and a plunger key. The plunger may comprise a rail and a keyway, and the plunger key may comprise a key guide coupled to the key track, an arm coupled to the key guide, and a rail slot through the arm. The arm may be disposed through the keyway of the plunger to allow the arm to move along the key track from a first position to a second position. The arm may be configured to block the rail in the first position and to align the rail slot with the rail in the second position so that the rail can move through the rail slot.

In more particular examples, a snap fitting may be movable with the arm from the first position to the second position and configured to be coupled to the housing in the second position to prevent return of the arm toward the first position. A snap fitting may additionally, or alternatively, may be configured to be coupled to the housing in the first position to prevent the arm from being removed from the keyway.

In other aspects, an apparatus for locking a plunger may comprise a key guide configured to move along a key track of an implant delivery system, a crossbar coupled to the key guide, an arm coupled to a first end of the crossbar, a first snap fitting coupled to the arm distal to the crossbar, a second snap fitting coupled to a second end of the crossbar, and a rail slot through the arm. The crossbar can be coupled to the key guide to allow the arm to move from a first position to a second position relative to the key track. In the first position, the arm can be configured to prevent movement of the plunger through the rail slot. In the second position, the arm can be configured to allow movement of the plunger through the rail slot. The first snap fitting and the second snap fitting can be configured to prevent the arm from returning to the first position from the second position.

In some embodiments, an apparatus for eye surgery may comprise a housing comprising a key track, a first catch, and a second catch; a bore through the housing; a plunger at least partially disposed in the bore, the plunger comprising a rail and a keyway; and a plunger key. The plunger key may comprise a key guide configured to slidingly engage the key track, a crossbar coupled to the key guide, a first cantilever arm coupled to the crossbar and disposed through the keyway, a first snap fitting coupled to the first cantilever arm distal to the crossbar, a second cantilever arm coupled to the crossbar, a second snap fitting coupled to the crossbar, and a rail slot through the first cantilever arm. The first cantilever arm and the second cantilever arm can be movable with the crossbar from a first position to a second position parallel to the key track. In the first position, the first cantilever arm can be configured to prevent movement of the rail through the rail slot, the first snap fitting can be configured to engage the first catch to prevent removal of the first cantilever arm from the keyway, and the second snap fitting can be configured to engage the second catch to prevent removal of the first cantilever arm from the keyway. In the second position, the first cantilever arm can be configured to allow movement of the rail through the rail slot, the first snap fitting can be configured to engage the first catch to prevent return of the first cantilever arm from the second position to the first position, and the second snap fitting is configured to engage the second catch to prevent return of the second cantilever arm from the second position to the first position.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
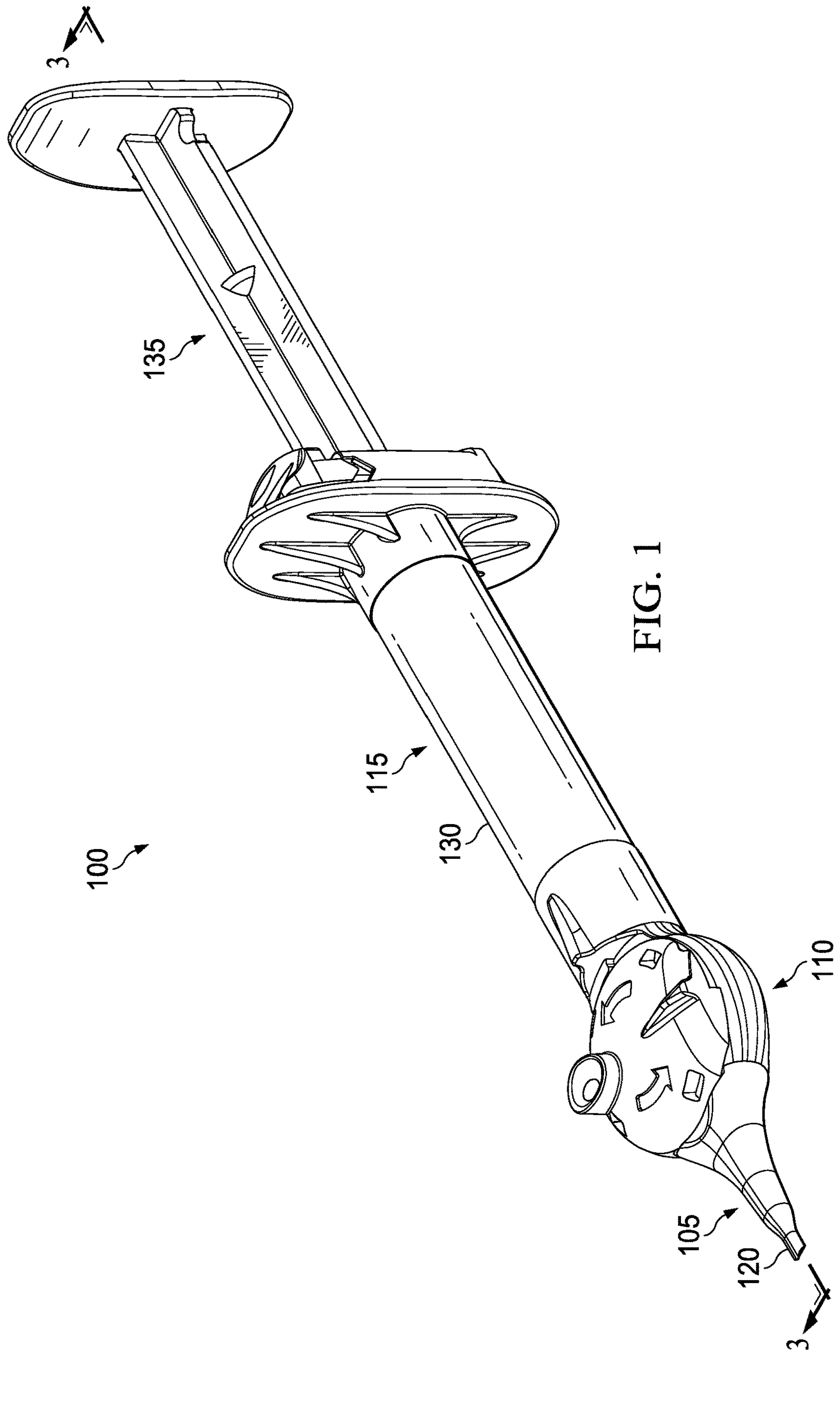
FIG. 1 is an auxiliary view of an example apparatus for delivering an implant into an eye.

FIG. 1 is an auxiliary view of an example of an apparatus 100 that can deliver an implant into an eye. In some embodiments, the apparatus 100 may comprise two or more modules, which can be configured to be coupled and decoupled as appropriate for storage, assembly, use, and disposal. As illustrated in FIG. 1, some embodiments of the apparatus 100 may include a nozzle 105, an implant bay 110 coupled to the nozzle 105, and an actuator 115 coupled to the implant bay 110.

The nozzle 105 generally comprises a tip 120 adapted for insertion through an incision into an eye. The size of the tip 120 may be adapted to surgical requirements and techniques as needed. For example, small incisions are generally preferable to reduce or minimize healing times. Incisions of less than 2 millimeters may be preferable in some instances, and the tip 120 of the nozzle 105 may have a width of less than 2 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may be configured to fold, tuck, extend or splay one or more features, such as haptics, of an intraocular lens.

The actuator 115 is generally configured to advance an implant from the implant bay 110 into the nozzle 105, and thereafter from the nozzle 105 through an incision and into an eye. The actuator 115 of FIG. 1 generally comprises a housing 130 and a plunger 135. The plunger 135 is generally comprised of a substantially rigid material, such as a medical grade polymer material.

In general, components of the apparatus 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the implant bay 110 may be mechanically coupled to the actuator 115 and may be mechanically and fluidly coupled to the nozzle 105. In some embodiments, components may also be coupled by virtue of physical proximity, being integral to a single structure, or being formed from the same piece of material.

Figure 2:
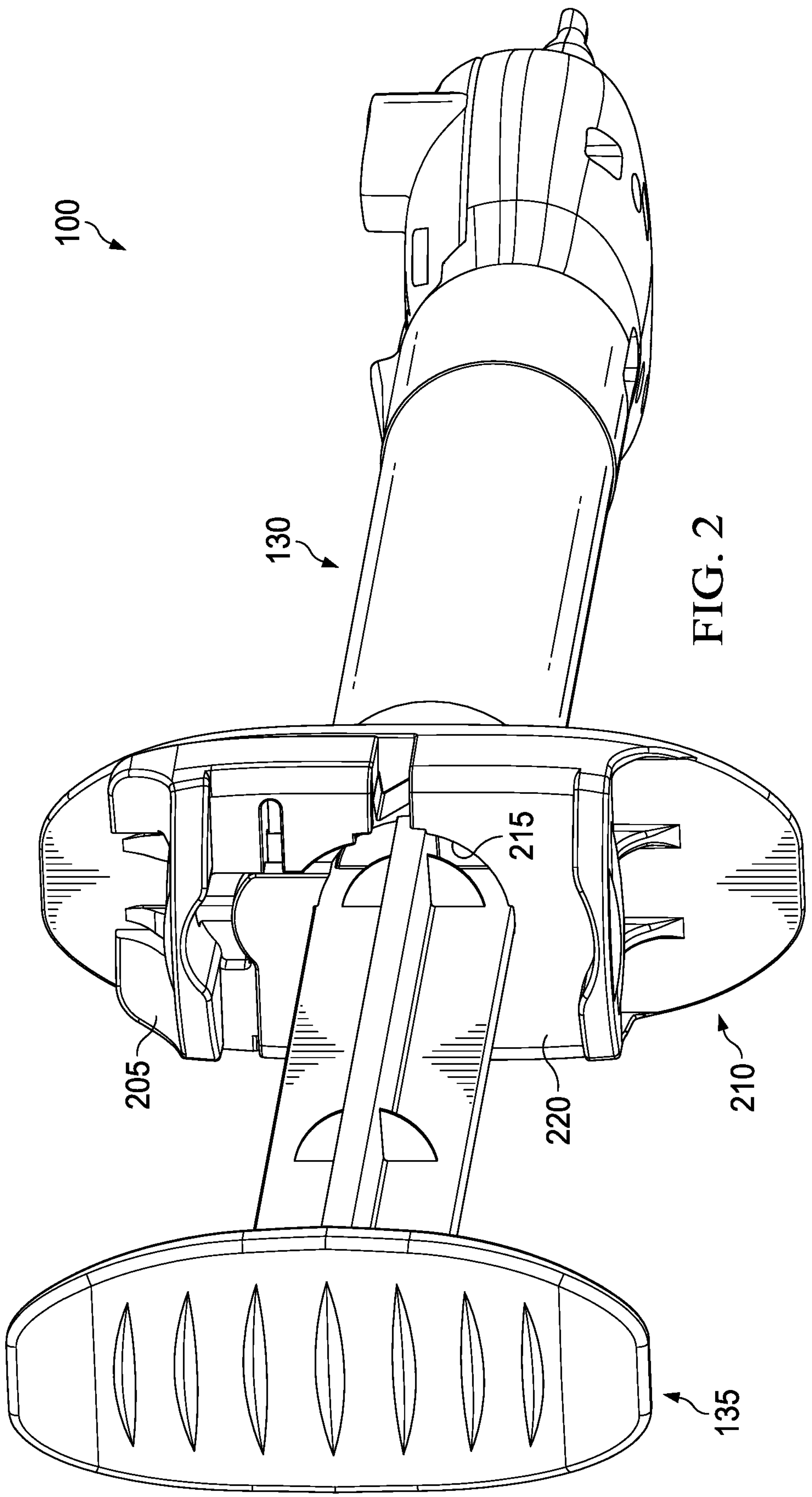
FIG. 2 is another auxiliary view of the apparatus of FIG. 1.

FIG. 2 is another auxiliary view of the apparatus 100, illustrating additional details that may be associated with some embodiments. For example, the apparatus 100 of FIG. 2 further comprises a plunger key 205, which may be coupled to a key mount 210 on the housing 130. The housing 130 generally has a bore 215 configured to receive the plunger 135 through the key mount 210. Some embodiments of the key mount 210 may further comprise a key box 220 configured to receive a portion of the plunger key 205, as illustrated in the example of FIG. 2.

Figure 3:
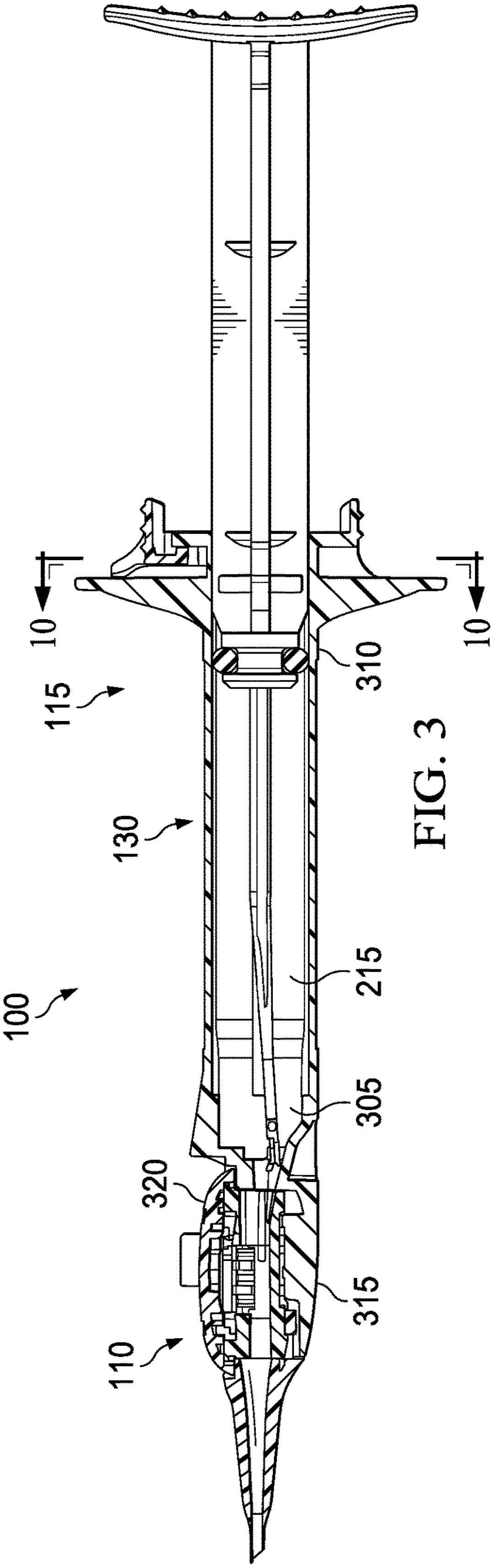
FIG. 3 is a section view of the apparatus of FIG. 1.

FIG. 3 is a section view of the apparatus 100 of FIG. 1, illustrating additional details that may be associated with some embodiments. For example, the bore 215 of FIG. 3 generally passes through the housing 130 longitudinally from a first end 305 to a second end 310, and the plunger 135 is disposed at least partially within the bore 215. In some examples, the implant bay 110 may comprise a base 315 and a cap 320, which may be coupled to the base 315. The base 315 may extend from or be coupled to actuator 115 in some examples. In FIG. 3, for example, the base 315 is coupled to the housing 130 proximate to the first end 305.

Figure 4:
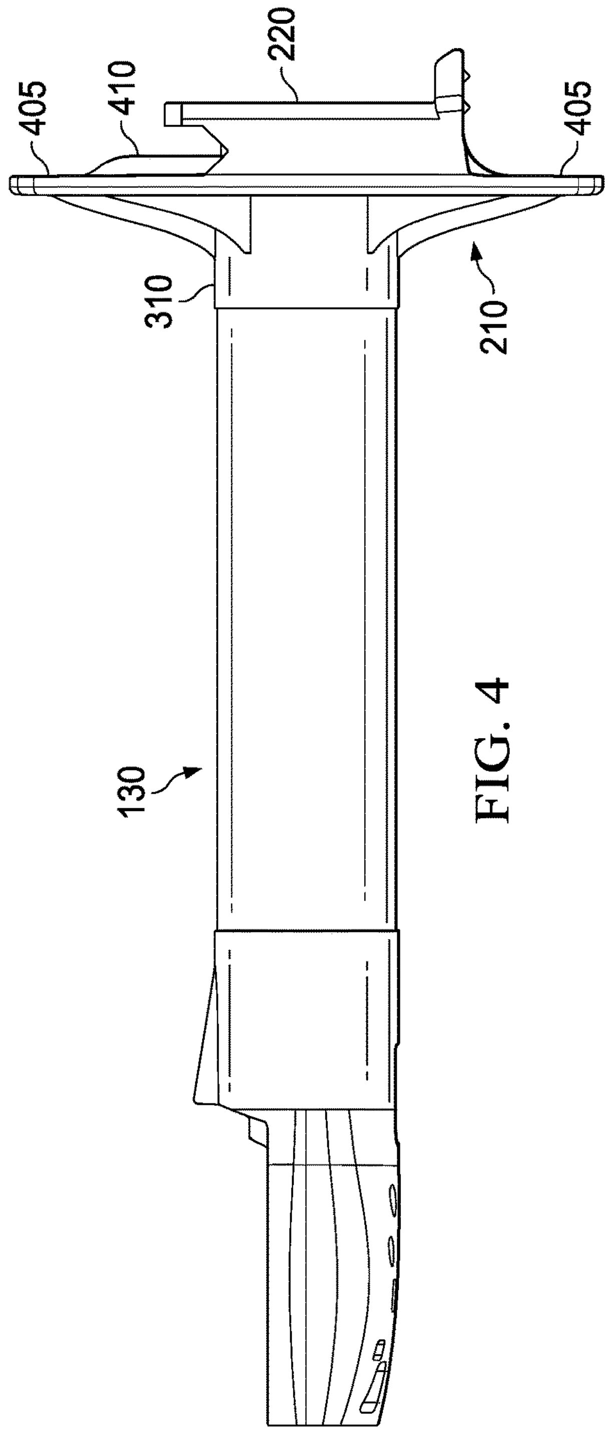
FIG. 4 is a front view of a housing that may be associated with some embodiments of the apparatus of FIG. 1.

FIG. 4 is a front view of the housing 130 of FIG. 1, illustrating additional details that may be associated with some embodiments. In some embodiments, the key mount 210 may be coupled to the second end 310 of the housing 130. For example, the key mount 210 of FIG. 4 generally comprises a flange 405, which is coupled to the second end 310 of the housing 130. The key mount 210 may additionally comprise a key track 410. In some embodiments, the key track 410 may comprise or consist essentially of a ridge or rail, as in the example of FIG. 4. In other examples, the key track 410 may comprise or consist essentially of a channel or groove in the key mount 210. As shown in the example of FIG. 4, some embodiments of the key box 220 may be coupled to and extend from the flange 405.

Figure 5:
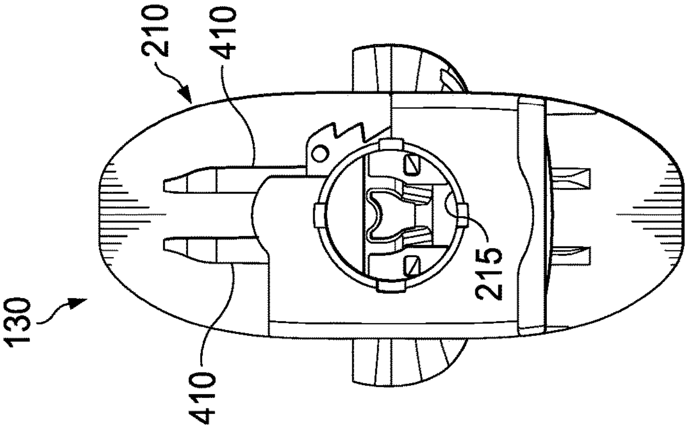
FIG. 5 is a side view of the housing of FIG. 4.

FIG. 5 is a side view of the housing 130 of FIG. 4, illustrating additional details that may be associated with some embodiments. For example, some embodiments of the key mount 210 may have more than one key track 410. In the example of FIG. 4, the key mount 210 comprises a first key track 410 and a second key track 410, which are mutually parallel to each other and generally orthogonal to the longitudinal direction of the bore 215.

Figure 6:
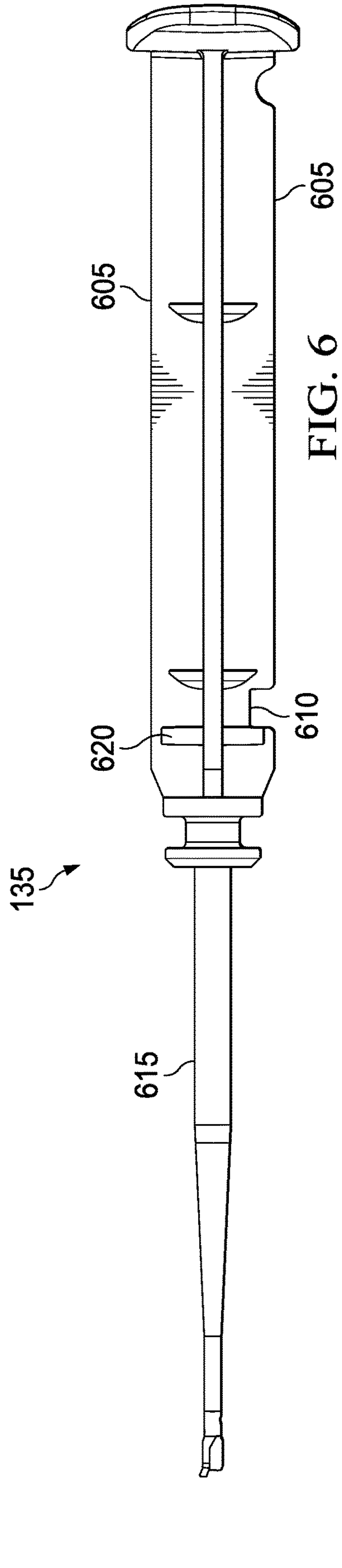
FIG. 6 is a top view of an example of a plunger that may be associated with some embodiments of the apparatus of FIG. 1.

FIG. 6 is a top view of an example of the plunger 135, illustrating additional details that may be associated with some embodiments. As illustrated in the example of FIG. 6, the plunger 135 may comprise one or more ridges, rails, or similar features, such as a rail 605, and a keyway 610. In general, each of the rails runs lengthwise along a portion of the plunger 135. In the example of FIG. 6, one end of the plunger 135 further comprises an implant interface 615, and the rail 605 runs lengthwise along the plunger 135 between the implant interface 615 and the opposite end of the plunger 135. In some examples, the keyway 610 may be disposed in one of the rails. For example, the keyway 610 may be a channel, groove, slot, notch, or similar feature in one of the rails. As show in FIG. 6, some embodiments of the keyway 610 may be disposed through the rail 605. Some embodiments of the plunger 135 may additionally comprise a plunger stop, such as a stop 620 illustrated in the example of FIG. 6.

Figure 7:
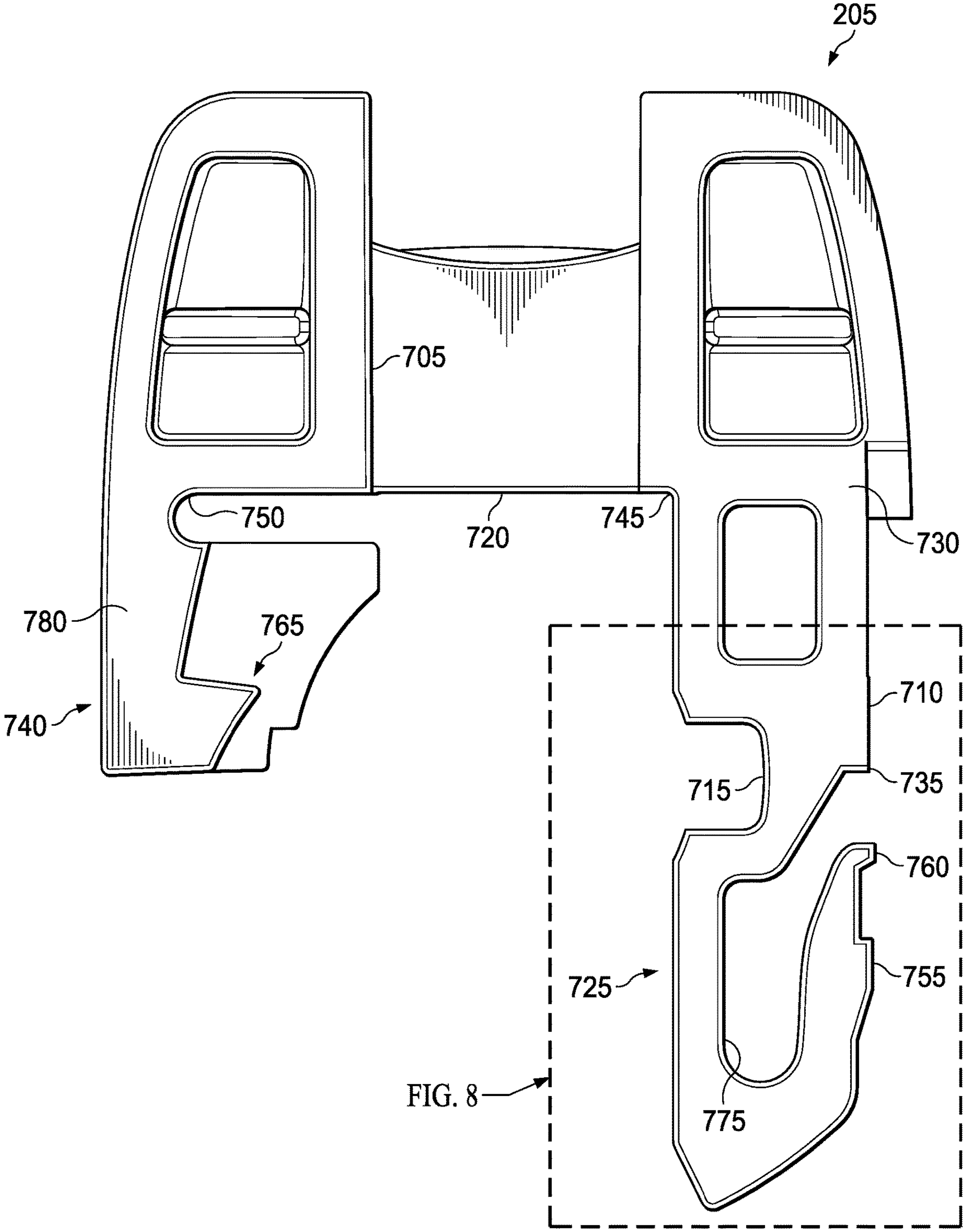
FIG. 7 is a side view of an example of a plunger key that may be associated with some embodiments of the apparatus of FIG. 1.

FIG. 7 is a side view of an example of the plunger key 205, illustrating additional details that may be associated with some embodiments. The plunger key 205 of FIG. 7 generally comprises a key guide 705, an arm 710, and a rail slot 715 through the arm 710. As illustrated in the example of FIG. 7, the arm 710 may be coupled to the key guide 705. In some examples, the plunger key 205 may comprise a crossbar 720. As illustrated in FIG. 7, the arm 710 may be indirectly coupled to the key guide 705 in some embodiments. More particularly, in some embodiments, the arm 710 may be coupled to one end of the crossbar 720, which may be coupled to the key guide 705.

In some embodiments, the plunger key 205 may additionally comprise one or more snap fittings. For example, the plunger key 205 of FIG. 7 comprises a first snap fitting 725, which may be coupled to the crossbar 720 in some embodiments. In more particular examples, the arm 710 may have a first end 730 coupled to the crossbar 720, and the first snap fitting 725 may be coupled to a second end 735 of the arm 710 distal to the crossbar 720. The plunger key 205 may additionally comprise a second snap fitting 740 in some embodiments. As illustrated in the example of FIG. 7, the second snap fitting 740 may be coupled to the crossbar 720 in some embodiments. The first snap fitting 725 of FIG. 7 is coupled to a first end 745 of the crossbar 720, and the second snap fitting 740 of FIG. 7 is coupled to a second end 750 of the crossbar 720. In some examples, a snap fitting may be curved, such as the first snap fitting 725 of FIG. 7. In more particular examples, the first snap fitting 725 has a curved end distal to the crossbar 720, as illustrated in FIG. 7.

A snap fitting generally comprises a hook, which may comprise or consist of a stud, bead, protrusion, overhand, catch, undercut, or similar feature or combination of similar features, which is coupled to a base and can be deformed or deflected to engage a joining feature on another component before returning to an unstressed state. In the example of FIG. 7, the first snap fitting 725 comprises a first hook 755 and a second hook 760, and the second snap fitting 740 comprises a third hook 765. The first hook 755 of FIG. 7 is disposed distal to the crossbar 720, relative to the second hook 760. A snap fitting may also be torsional, annular, or cantilevered in various embodiments. In FIG. 7, the first snap fitting 725 and the second snap fitting 740 are both examples of a cantilever snap fitting, in which a cantilever couples the hook to the base. More particularly, the first snap fitting 725 of FIG. 7 comprises a cantilever 775 that couples the first hook 755 and the second hook 760 to the arm 710, which is representative of a base for the first snap fitting 725 in this example. The cantilever 775 of FIG. 7 is a curved cantilever. The second snap fitting 740 comprises a cantilever 780 that couples the third hook 765 to the crossbar 720, which is representative of a base for the second snap fitting 740 in this example.

Figure 8:
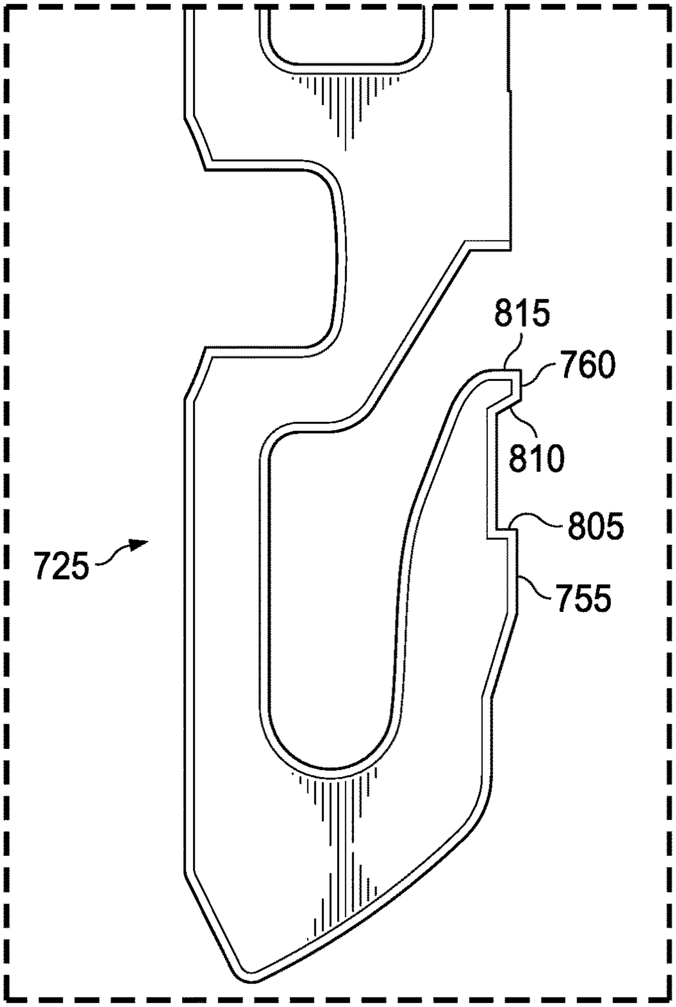
FIG. 8 is a detail view of a snap fitting that may be associated with the plunger key of FIG. 7.

FIG. 8 is a detail view of the first snap fitting 725 of FIG. 7. Generally, a snap fitting may comprise a lead surface, which can be configured to cause deformation or deflection in response to movement in a first direction relative to a joining feature. A trailing surface can likewise be configured to cause deformation or deflection in response to movement in a second direction relative to the joining feature. The second direction is generally opposite to the first direction. In more specific examples, a trailing surface may be a locking surface, which can be configured to make deformation or deflection relatively difficult, thereby discouraging or preventing separation after the snap fitting has been joined to another component. In the example of FIG. 8, the first hook 755 comprises a first locking surface 805. The second hook 760 of FIG. 8 comprises a lead surface 810 and a second locking surface 815.

Figure 9:
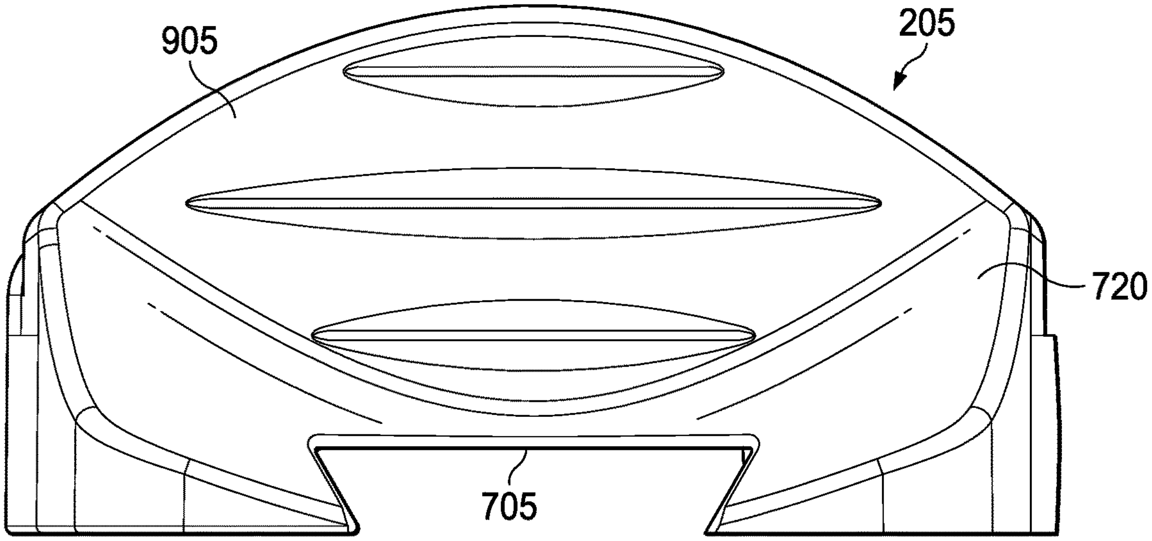
FIG. 9 is a top view of the plunger key of FIG. 7.

FIG. 9 is a top view of the plunger key 205 of FIG. 7, illustrating additional details that may be associated with some embodiments. For example, as illustrated in FIG. 7, some embodiments of the key guide 705 may comprise or consist essentially of a channel through the crossbar 720. In other examples, the key guide 705 may comprise or consist essentially of one or more ridges, rails, bars, or similar features coupled to the crossbar 720. In some embodiments, the plunger key 205 may further comprise a finger flange 905, which can be coupled to the crossbar 720 as illustrated in the example of FIG. 9.

Figure 10A:
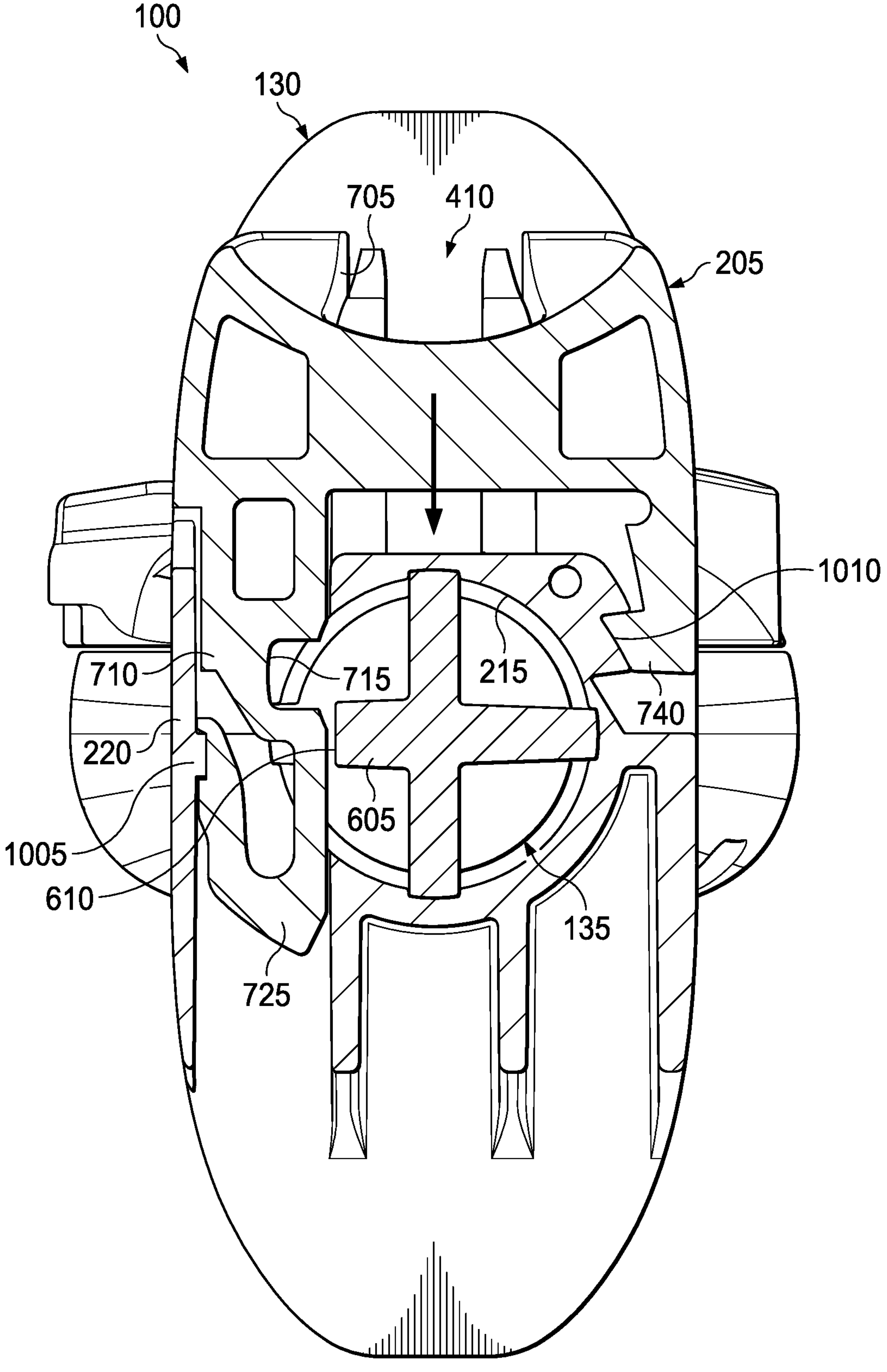
FIG. 10A and FIG. 10B are section views of the apparatus of FIG. 3, taken along section line 10-10.
Figure 10B:
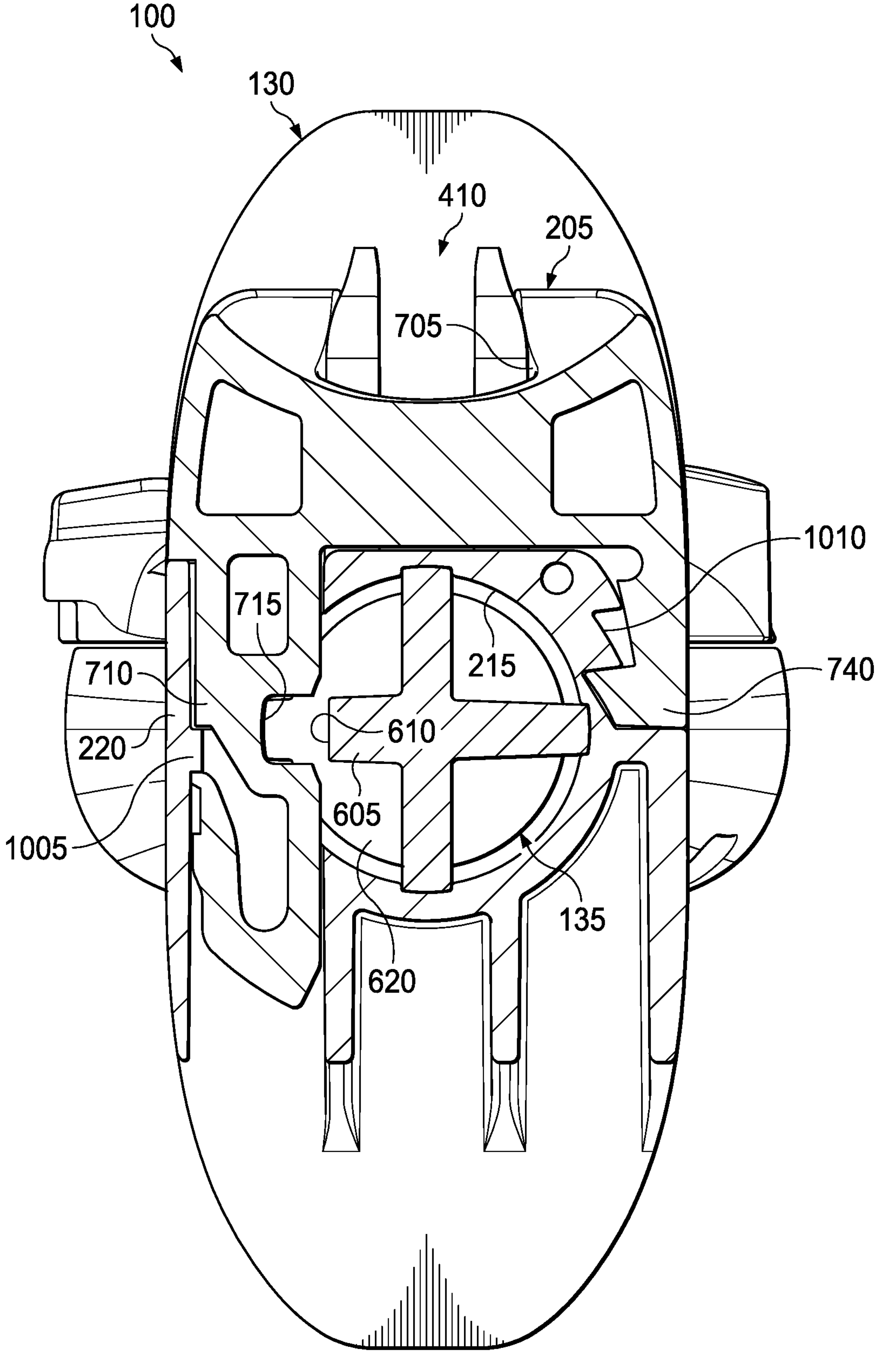

FIG. 10A and FIG. 10B are section views of the apparatus 100 of FIG. 3, taken along section line 10-10. FIG. 10A illustrates additional details that may be associated with some embodiments of the apparatus 100 in a first state, and FIG. 10B illustrates additional details that may be associated with some embodiments of the apparatus 100 in a second state. For example, FIG. 10A and FIG. 10B both illustrate an embodiment of the key track 410, the bore 215 through the housing 130, the plunger 135 at least partially disposed in the bore 215, the plunger key 205, and the arm 710 coupled to the key guide 705. In the example of FIG. 10A and FIG. 10B, the key track 410 comprises a pair of parallel track rails, which are generally oriented orthogonal to the bore 215. The key guide 705 may be coupled to the key track 410, as illustrated in the example of FIG. 10A and FIG. 10B. FIG. 10A and FIG. 10B also illustrate an embodiment of the housing 130 having a first catch 1005 and a second catch 1010.

In the example of FIG. 10A, the key guide 705 is configured to slidingly engage the key track 410, which can allow the plunger key 205 to move in a first direction toward the bore 215 while substantially preventing lateral movement of the plunger key 205 relative to the key track 410. The arm 710 of FIG. 10A is disposed through the keyway 610 of the plunger 135, and movement of the key guide 705 relative to the key track 410 can also move the arm 710 through the keyway 610 from a first position, illustrated in the example of FIG. 10A, to a second position, illustrated in the example of FIG. 10B.

In the first position, the arm 710 is configured to block the rail 605. More particularly, the arm 710 can pass through the keyway 610 so that the rail slot 715 is offset from the rail 605, thereby preventing the rail 605 (and, thus, the plunger 135) from moving through the rail slot 715 relative to the bore 215. In the context of the example of FIG. 10A and FIG. 10B, the first position is a locked position.

In the second position of FIG. 10B, the rail slot 715 is aligned with the rail 605 so that the rail 605 can move through the rail slot 715, thereby allowing the rail 605 and the plunger 135 to move relative to the bore 215. In the context of the example of FIG. 10A and FIG. 10B, the second position is an unlocked position. In the unlocked position, the arm 710 may also be configured to block the stop 620 in some embodiments, as illustrated in the example of FIG. 10B. In the unlocked position, the arm 710 can allow bidirectional movement of the plunger 135 within the bore 215, while the stop 620 can limit such movement in one direction, thereby preventing the plunger 135 from being completely removed from the bore 215.

In the example of FIG. 10A and FIG. 10B, the first snap fitting 725 is movable with the arm 710 from the first position to the second position. In some embodiments, the first snap fitting 725 may be configured to be coupled to the housing 130 in the second position to prevent return of the arm 710 from the second position toward the first position, thereby maintaining alignment of the rail slot 715 with the rail 605 and substantially reducing or eliminating the risk of inadvertent locking of the plunger 135 after it is unlocked. In more particular embodiments, the first snap fitting 725 may be configured to engage the first catch 1005 to prevent return of the arm 710. Additionally, or alternatively, the first snap fitting 725 may be configured to be coupled to the housing 130 in the first position to prevent movement of the arm 710 in a second direction, such as away from the bore 215 in the example of FIG. 10A, thereby substantially reducing or eliminating the risk of inadvertent removal of the arm 710 from the keyway 610. More generally, the first snap fitting 725 may be configured to be coupled to the housing 130 in the first position, the second position, or both, which can substantially reduce or eliminate the risk of inadvertent removal of the plunger key 205 from the housing 130.

Additionally, or alternatively, in some embodiments, the second snap fitting 740 may be configured to prevent the arm 710 from returning to the first position from the second position. For example, the second snap fitting 740 of FIG. 10B is configured to engage the second catch 1010 to prevent movement of the arm 710 away from the second position. Some embodiments of the second snap fitting 740 may also be configured to be coupled to the housing 130 in the first position to prevent movement of the arm 710 in the second direction, such as away from the bore 215 in the example of FIG. 10A. For example, the second catch 1010 may comprise more than one undercut or stop, and the second snap fitting 740 may be configured to engage a first stop in the first position and a second stop in the second position.

Movement of the plunger key 205 in the example of FIG. 10A and FIG. 10B can be constrained by various features of the apparatus 100. More particularly, various features may constrain movement of the arm 710 and the rail slot 715 relative to the key track 410. For example, the key track 410 and the key guide 705 of FIG. 10A and FIG. 10B can allow the arm 710 and the rail slot 715 to move parallel to the key track 410, while substantially preventing orthogonal movement. In some embodiments, such as the example of FIG. 10A and FIG. 10B, the key box 220 can further support and constrain movement of the arm 710 and the rail slot 715 parallel to the key track 410. In the example of FIG. 10A and FIG. 10B, the key track 410 generally extends orthogonal to the plunger 135 and, more particularly, to the rail 605. Such constrained motion can provide reliable interaction between the plunger 135 and the plunger key 205.

Additionally, or alternatively, the first snap fitting 725, the second snap fitting 740, or both, can provide stability, tactile feedback, and/or audible feedback. For example, either or both of the first snap fitting 725 and the second snap fitting 740 may increase the stability of the plunger key 205 by preventing or deterring removal of the plunger key 205 from the key mount 210. Either or both may also provide tactile feedback by resisting movement of the plunger key 205 from the locked position of FIG. 10A to the unlocked position of FIG. 10B, thereby reducing the risk of inadvertently unlocking the plunger 135. Either or both may additionally provide audible feedback as they snap into the second position.

Figure 11:
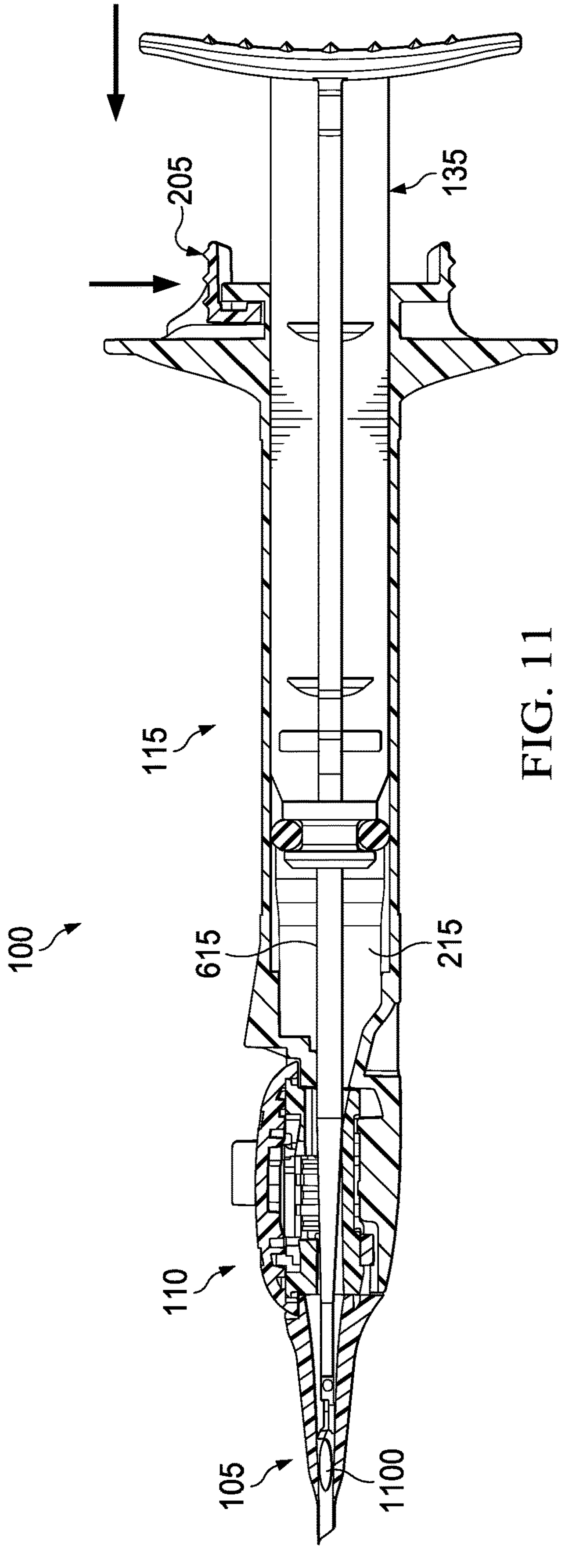
FIG. 11 is a schematic diagram illustrating an example method of ejecting an implant from the apparatus of FIG. 1.

FIG. 11 is a schematic diagram illustrating an example method of ejecting an implant 1100 from the apparatus 100. Initially, various components of the system may be assembled if needed or appropriate. In the example of FIG. 11, the nozzle 105, the implant bay 110, and the actuator 115 are fixed together to form a unitary structure. In other embodiments, the apparatus 100 may comprise two or more modules, which can be configured to be coupled and decoupled as appropriate for storage, assembly, use, and disposal.

In the example of FIG. 11, the plunger key 205 is placed in the second, unlocked position, substantially as described with reference to FIG. 10B, which allows the plunger 135 to be advanced through the bore 215 toward the implant bay 110 as shown.

The implant 1100 may be stored initially in the implant bay 110. In some embodiments, the implant bay 110 may additionally or alternatively be configured to prepare the implant 1100 for delivery. For example, some embodiments of the implant bay 110 may be configured to be actuated by a surgeon or other operator to prepare the implant 1100 for delivery by subsequent action of the actuator 115. In some instances, the implant bay 110 may be configured to actively deform, elongate, extend, or otherwise manipulate features of the implant 1100 before the implant 1100 is advanced into the nozzle 105. For example, some embodiments of the implant bay 110 may be configured to orient or fold an implant. Some embodiments of the implant 1100 may comprise one or more haptics, which can be oriented or folded for delivery.

In some embodiments, the implant interface 615 can be configured to contact or otherwise engage the implant 1100 to advance the implant 1100 from the implant bay 110 through the nozzle 105 as the plunger 135 is advanced. As illustrated in the example of FIG. 11, at least a portion of the implant interface 615 may extend into or through the implant bay 110 and/or the nozzle 105. As the plunger 135 is fully advanced, the implant interface 615 can eject the implant 1100 from the nozzle 105.

Figure 12A:
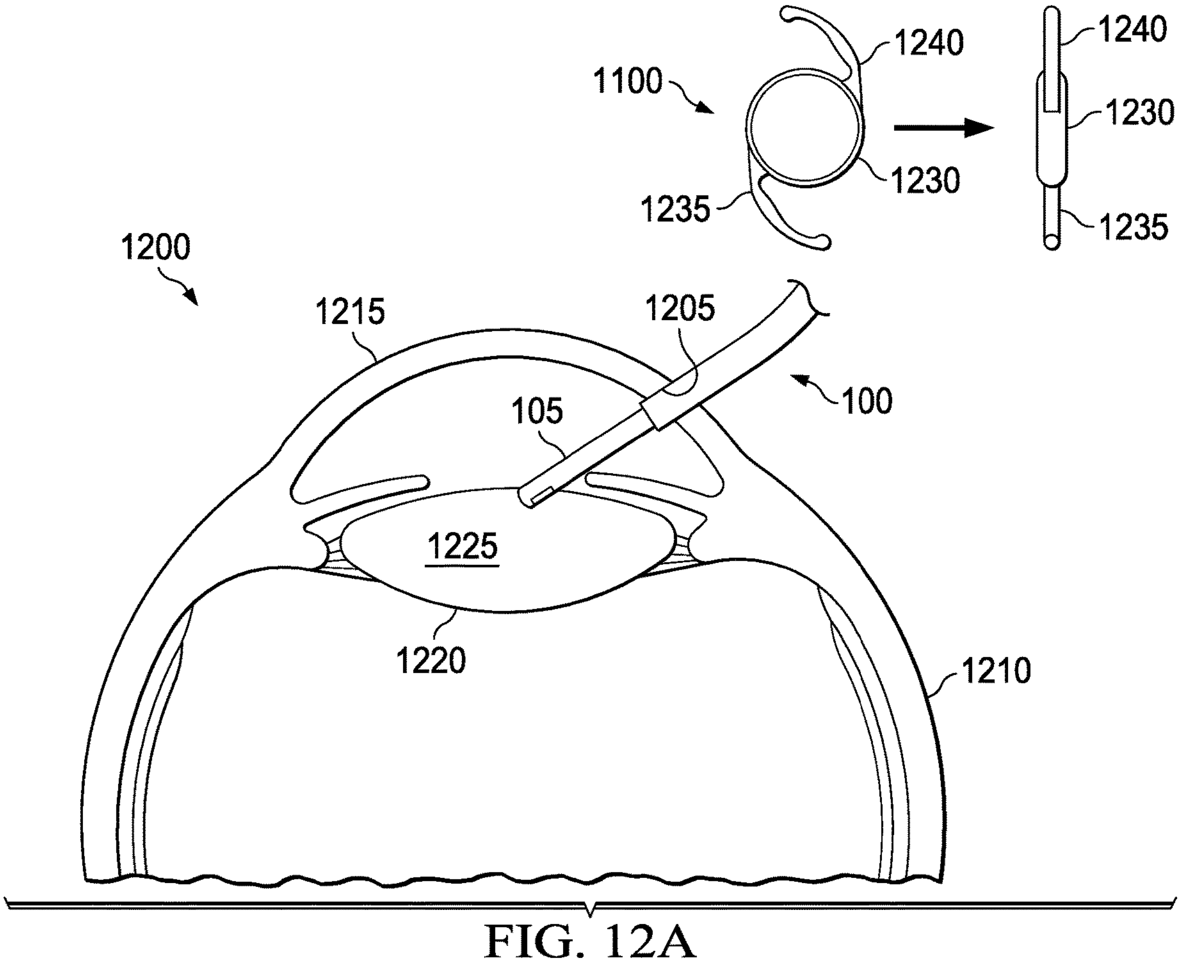
FIG. 12A and FIG. 12B are schematic diagrams illustrating an example use of the apparatus of FIG. 11 to deliver an implant to an eye.
Figure 12B:
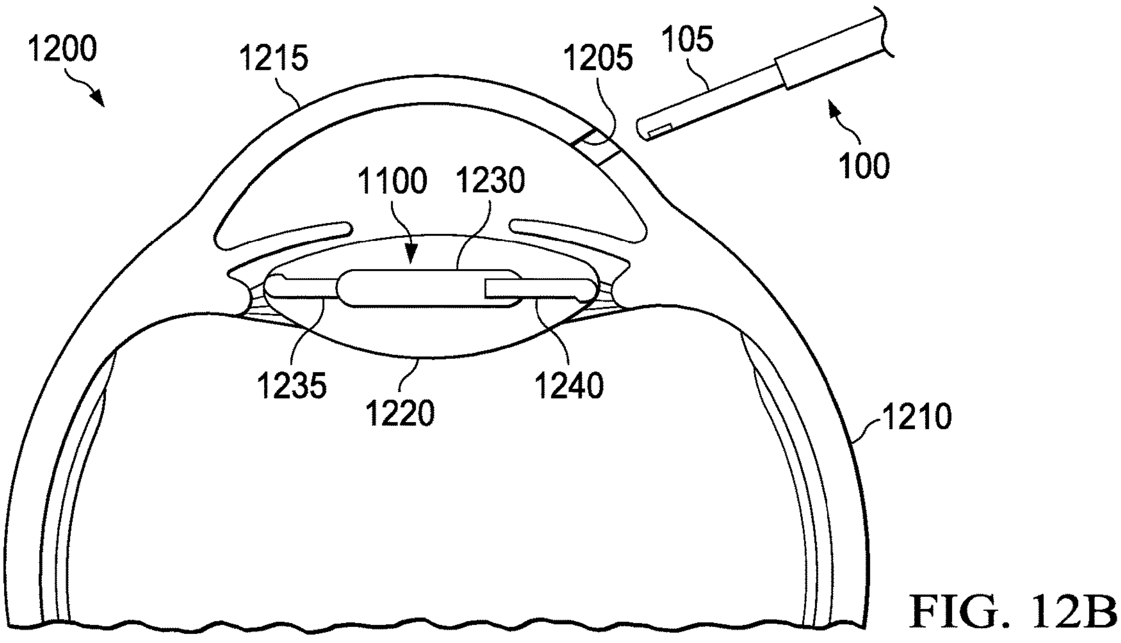

FIG. 12A and FIG. 12B are schematic diagrams illustrating an example use of the apparatus 100 of FIG. 11 to deliver the implant 1100 to an eye 1200. As illustrated, an incision 1205 may be made in the eye 1200 by a surgeon, for example. In some instances, the incision 1205 may be made through the sclera 1210 of the eye 1200. In other instances, an incision may be formed in the cornea 1215 of the eye 1200. The incision 1205 may be sized to permit insertion of a portion of the nozzle 105 to deliver the implant 1100 into the capsular bag 1220. For example, in some instances, the size of the incision 1205 may have a length less than about 3000 microns (3 millimeters). In other instances, the incision 1205 may have a length of from about 1000 microns to about 1500 microns, from about 1500 microns to about 2000 microns, from about 2000 microns to about 2500 microns, or from about 2500 microns to about 3000 microns.

After the incision 1205 is made, the nozzle 105 can be inserted through the incision 1205 into an interior portion 1225 of the eye 1200. The apparatus 100 can then eject the implant 1105 through the nozzle 105 into the capsular bag 1220 of the eye 1200, substantially as described with reference to FIG. 11.

In some embodiments, the implant 1100 may comprise an intraocular lens having a shape similar to that of a natural lens of an eye, and it may be made from numerous materials. Examples of suitable materials may include silicone, acrylic, and combinations of such suitable materials. In some instances, the implant 1100 may comprise an intraocular lens that is fluid-filled, such as a fluid-filled accommodating intraocular lens. The implant 1100 may also comprise an intraocular lens that includes one or more features, such as haptics, for positioning the intraocular lens within an eye. In the example of FIG. 12A and FIG. 12B, the implant 1100 is illustrative of an intraocular lens having an optic body 1230, a leading haptic 1235, and a trailing haptic 1240.

The implant 1100 may be delivered in a folded configuration and can revert to a resting state with the leading haptic 1235 and the trailing haptic 1240 being at least partially curved around the optic body 1230, within the capsular bag 1220, as shown in FIG. 12B. The capsular bag 1220 can retain the implant 1100 within the capsular bag 1220 in a relationship relative to the eye 1200 so that the optic body 1230 refracts light directed to the retina (not shown). The leading haptic 1235 and the trailing haptic 1240 can engage the capsular bag 1220 to secure the implant 1100 therein. After delivering the implant 1100 into the capsular bag 1220, the nozzle 105 may be removed from the eye 1200 through the incision 1205, and the eye 1200 can be allowed to heal over time.

The systems, apparatuses, and methods described herein may provide significant advantages. Some embodiments may be particularly advantageous for delivering intraocular lenses, providing increased reliability and consistency for implant delivery. For example, the plunger key 205 can be placed in a stable, locked position before implant delivery and then moved into a stable, unlocked position to allow the plunger 135 to deliver an implant. In the locked position, the apparatus 100 can substantially reduce or eliminate the risk of accidental movement of the plunger, which can cause premature ejection of an implant or other undesirable results. In the unlocked position, the apparatus 100 can substantially reduce or eliminate the risk of accidental removal of the plunger 135, as well as accidental return to the locked position during implant delivery.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may also be combined or eliminated in various configurations for purposes of sale, manufacture, assembly, or use. For example, in some configurations, housing 130, the plunger 135, and the plunger key 205 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for eye surgery, the apparatus comprising:
a housing comprising a key track;
a bore through the housing;
a plunger at least partially disposed in the bore, the plunger comprising a rail and a keyway; and
a plunger key, the plunger key comprising:
a key guide coupled to the key track,
an arm coupled to the key guide, the arm disposed through the keyway of the plunger to allow the arm to move along the key track from a first position to a second position, and
a rail slot through the arm;
wherein the arm is configured to block the rail in the first position and to align the rail slot with the rail in the second position so that the rail can move through the rail slot.

2. The apparatus of claim 1, further comprising a snap fitting, the snap fitting movable with the arm from the first position to the second position and configured to be coupled to the housing in the second position to prevent return of the arm toward the first position.

3. The apparatus of claim 1, further comprising a snap fitting, the snap fitting movable with the arm from the first position to the second position and configured to be coupled to the housing in the first position to prevent the arm from being removed from the keyway and in the second position to prevent return of the arm toward the first position.

4. The apparatus of claim 2, wherein the snap fitting is a cantilever snap fitting.

5. The apparatus of claim 4, wherein the snap fitting is curved.

6. The apparatus of claim 2, wherein the snap fitting is coupled to the arm.

7. The apparatus of claim 1, wherein the keyway is disposed through the rail.

8. The apparatus of claim 1, wherein:
the plunger further comprises a stop; and
the arm is configured to engage the stop to prevent removal of the plunger from the bore.

9. An apparatus for locking a plunger of an implant delivery system, the apparatus comprising:
a key guide configured to move along a key track of the implant delivery system;
a crossbar coupled to the key guide, the crossbar having a first end and a second end;
an arm coupled to the first end of the crossbar;
a first snap fitting coupled to the arm distal to the crossbar;
a second snap fitting coupled to the second end of the crossbar; and
a rail slot through the arm;
wherein the crossbar is coupled to the key guide to allow the arm to move from a first position to a second position relative to the key track, the first position is configured to prevent movement of the plunger through the rail slot, the second position is configured to allow movement of the plunger through the rail slot, and the first snap fitting and the second snap fitting are configured to prevent the arm from returning to the first position from the second position.

10. The apparatus of claim 9, wherein the first snap fitting is a cantilever snap.

11. The apparatus of claim 10, wherein the cantilever snap has a curved end distal to the crossbar.

12. The apparatus of claim 9, wherein the first snap fitting further comprises a first hook distal to the crossbar and a second hook proximal to the crossbar, and the first hook and the second hook are configured to be coupled to the implant delivery system.

13. The apparatus of claim 12, wherein the first hook comprises a locking surface configured to be coupled to the implant delivery system in the first position.

14. The apparatus of claim 12, wherein the second hook comprises a locking surface configured to be coupled to the implant delivery system in the second position.

15. The apparatus of any of claim 12, wherein the second hook comprises:

a lead surface configured to contact the implant delivery system in the first position; and a locking surface configured to be coupled to the implant delivery system in the second position.

16. The apparatus of claim 9, wherein the rail slot comprises a channel through the arm.

17. The apparatus of claim 9, wherein the key guide comprises a channel through the crossbar.

18. An apparatus for eye surgery, the apparatus comprising:

a housing comprising a key track, a first catch, and a second catch;

a bore through the housing;

a plunger at least partially disposed in the bore, the plunger comprising a rail and a keyway; and a plunger key, the plunger key comprising:

a key guide configured to slidingly engage the key track, a crossbar coupled to the key guide, a first cantilever arm coupled to the crossbar and disposed through the keyway, a first snap fitting coupled to the first cantilever arm distal to the crossbar, a second cantilever arm coupled to the crossbar, a second snap fitting coupled to the crossbar, and a rail slot through the first cantilever arm;

wherein the first cantilever arm and the second cantilever arm are movable with the crossbar from a first position to a second position parallel to the key track;

in the first position, the first cantilever arm is configured to prevent movement of the rail through the rail slot, the first snap fitting is configured to engage the first catch to prevent removal of the first cantilever arm from the keyway, and the second snap fitting is configured to engage the second catch to prevent removal of the first cantilever arm from the keyway; and in the second position, the first cantilever arm is configured to allow movement of the rail through the rail slot, the first snap fitting is configured to engage the first catch to prevent return of the crossbar from the second position to the first position, and the second snap fitting is configured to engage the second catch to prevent return of the crossbar from the second position to the first position.

* * * * *